(12) United States Patent
Anzalone (10) Patent No.: US 6,495,590 B1
(45) Date of Patent: Dec. 17, 2002

(54) USE OF AMTOLMETIN GUACYL FOR THE PRODUCTION OF ANTI-INFLAMMATORY DRUGS FOR INTESTINAL INFLAMMATIONS

(75) Inventor: Sergio Anzalone, Rome (IT)

(73) Assignees: Medosan Ricerca S.r.l., Cecchina (IT); Sigma-Tau Industrie Farmaceutiche Riunite S.p.A., Pomezia (IT)

( * ) Notice: Subject to any disclaimer, the term of this patent is extended or adjusted under 35 U.S.C. 154(b) by 0 days.

(21) Appl. No.: 09/857,432

(22) PCT Filed: Dec. 3, 1999

(86) PCT No.: PCT/IT99/00398

§ 371 (c)(1),
(2), (4) Date: Oct. 1, 2001

(87) PCT Pub. No.: WO00/32188

PCT Pub. Date: Jun. 8, 2000

(30) Foreign Application Priority Data

Dec. 3, 1998 (IT) .................................. RM98A0745

(51) Int. Cl.$^7$ .............................................. A61K 31/40
(52) U.S. Cl. ...................................................... 514/423
(58) Field of Search ........................................ 514/423

(56) References Cited

U.S. PATENT DOCUMENTS

| 5,866,600 A | * | 2/1999 | Anzalone | 514/423 |
| 5,889,041 A | * | 3/1999 | Anzalone | 514/423 |
| 6,180,658 B1 | * | 1/2001 | Anzalone | 514/423 |

FOREIGN PATENT DOCUMENTS

| EP | 0 755 679 A2 | 7/1996 |
| GB | 2 115 417 A A1 | 9/1983 |

OTHER PUBLICATIONS

M. Dore et al., "P-selectin- and CD18-mediated Recruitment of Canine Neutrophils under Conditions of Shear Stress", *Vet Pathol*, 1995, pp. 258–268, vol. 32.

M.W. Greaves et al., "Prostaglandins, Leukotrienes, Phospholipase, Platelet Activating Factor, and Cytokines: An Integrated Approach to Inflammation of Human Skin", *Arch Dermatol Res*, 1988, pp. S33–S41, vol. 280.

L. Fry, "Psoriasis", *British Journal of Dermatology*, 1988, pp. 445–461, vol. 119.

J.J.F. Belch, "Eicosanoids and Rheumatology: Inflammatory and Vascular Aspects", *Prostaglandins LeukotEssent Fatty Acids*, 1989, pp. 219–234, vol. 36.

A.W. Ford–Hutchinson, "Leukotrienes: Their Formation and Role as Inflammatory Mediators", *Fred Proc*, 1985, pp. 25–29, vol. 44, No. 1.

A.B. Kay et al., "Leukocytes in Asthma", *Immunol Invest*, 1988, pp. 690–705, vol. 17(8&9).

David Raeburn, "Eicosanoids, Epithelium and Airway Reactivity", *Gen. Pharmac*, 1990, pp. 11–16, vol. 21, No. 1.

A.R. Leff, "Toward the Formulation of a Theory of Asthma", *Perspective in Biology and Medicine*, 1990, pp. 292–302, vol. 33.

M. Mayer, "Effect of Calcium Ionophore A23187 and of Leukotrienes $B_4$ and $C_4$ on the Adherence of mononuclear Leucocytes in Multiple Sclerosis", *Folia Biologica (Praha)*, 1988, pp. 10–17, vol. 34.

William F. Stenson, "Arachidonic Acid Metabolites in Inflammatory Bowel Disease", *Adv Inflamm Res*, 1988, pp. 215–222, vol. 12.

R. Schumert et al., Role of Eicosanoids in Human and Experimental Colitis *Digestive Diseases and Sciences*, 1988, pp. 58S–64S, vol. 33, No. 3.

E.J. Goetzl et al., "generation and Recognition of Leukotriene Mediators of Hypersensitivity and Inflammation", *Digestive Diseases and Sciences*, 1988, pp. 36S–40S, vol. 33, No. 3.

K. Lauritsen et al., "Inflammatory Intermediaries in Inflammatory Bowel Disease", *Int J Colon Dis*, 1989, pp. 75–90, vol. 4.

J. Rask–Madsen et al., "Eicosanoids in Inflammatory Bowel Disease—Physiology and Pathology", In *The Cell Biology of inflammation in the gastrointestinal Tract*, T.J. Peters, Eds., 1990, pp. 255–271, Corners Publications.

N.K. Boughton–Smith et al., "Biosynthesis of Lipoxygenase and Cyclo–Oxygenase Products from [14C]–Arachidonic Acid by Human Colonic Mucosa", *Gut*, 1983, pp. 1176–1182, vol. 24.

Pinchas Sharon et al., "Enhanced Synthesis of Leukotriene $B_4$ by Colonic Mucosa in Inflammatory Bowel Disease", *Gastroenterology*, 1984, pp. 453–460, vol. 86.

S.R. Gould et al., "Studies of Prostaglandins and Sulphasalazine in Ulcerative Colitis", *Prostaglandins and Medicine*, 1981, pp. 165–182, vol. 6.

D.S. Hampton et al., "Prostaglandin Synthesis Inhibitors in Ulcerative Colitis", *Prostaglandins*, 1981, pp. 417–425, vol. 21.

G.J. Blackwell et al., "Macrocortin: A Polypeptide Causing the Anti–Phospholipase Effect of Glucocorticoids", *Nature*, 1980, pp. 147–149, vol. 287.

R.P. MacDermott et al., "Alterations of the Immune System in Ulcerative Colitis and Crohn's Disease", *Advances in Immunology*, 1988, pp. 285–328, vol. 42.

D.J. Fretland et al., "Eicosanoids and Inflammatory Bowel Disease: Regulation and Prospects for Therapy", *Prostaglandins Leukotrienes and Essential Fatty Acids*, 1990, pp. 215–233, vol. 41.

(List continued on next page.)

Primary Examiner—James H. Reamer
(74) Attorney, Agent, or Firm—Browdy and Neimark, P.L.L.C.

(57) ABSTRACT

The present invention relates to the use of amtolmetin guacyl for the production of an anti-inflammatory drug for intestinal inflammations. Furthermore, the uses of amtolmetin guacyl for the treatment of thrombophlebitis, as anti-platelet agent and for anti-inflammatory and antalgic treatment, particularly in the case of infracted subjects and of subjects suffering from an ictus of thrombotic type are disclosed.

7 Claims, 6 Drawing Sheets

OTHER PUBLICATIONS

E. Arrigoni–Martelli, "2–[2–[1–methyl–5–(4–methylbenzoyl)pyrrol–2–yl]acetamide]acetic acid 2–methoxyphenyl ester. MED–15", *Drugs of the Future*, 1989, pp. 963–965, vol. 14, No. 10.

E. Turbaro et al., "Studies on the Gastric Tolerability of the New Non–Steroidal Anti–inflammatory Drug Amtolmetin Guacyl", *Arzeim Forsch Drug Res*, 1995, pp. 1298–1302, vol. 45.

A. Szallasi et al., "Resiniferatoxin and Its Analogs Provide Novel Insights Into the Pharmacology of the Vanilloid (Capsaicin) Receptors", *Life Sciences*, 1990, pp. 1399–1408, vol. 47.

B.M. Peskar et al., "A Monoclonal Antibody to Calcitonin Gene–Related Peptide Abolishes Capsaicin–induced Gastroprotection", *European Journal of Pharmacology*, 1993, pp. 201–203, vol. 250.

J. Ren et al., "Calcitonin gene–related Peptide Mediates Capsaicin–induced Neuroendocrine Responses in Rat Antrum", *Gastroenterology*, 1993, pp. 485–491, vol. 104.

Y. Kinoshita et al., "Calcitonin Gene–related Peptide: A Neurotransmitter Involved in Capsaicin–Sensitive Afferent Nerve–mediated Gastric Mucosal Protection", *J Clin Gastroenterol*, 1993, pp. S27–S32, vol. 17.

P. Holzer et al., "Release of Calcitonin Gene–related Peptide Induced by Capsaicin in the Vasculary Perfused Rat Stomach", *Neuroscience Letters*, 1990, pp. 195–200, vol. 108.

K. Yagi et al., "Eff4ects of Pituitary Adenylate Cyclase Activating Polypeptide–27 On Alkaline Secretory and Mucosal Ulcerogenic Responses in Rat Duodenum", *Life Sciences*, 1998, pp. 317–325, vol. 63.

P. Holzer et al., "Sensory Nerves, Nitric Oxide and NANC Vasodilatation", *Arch. Int. Pharmacodyn*, 1995, pp. 67–79, vol. 329.

P. Holzer et al., "Vascular Bed–Dependent Roles of the Peptide CGRP and Nitric Oxide in Acid–Evoked Hyperaemia of the Rat Stomach", *Journal of Physiology*, 1994, pp. 575–585, vol. 480.

R. Mathison et al., "Regulation of Jejunal Arterioles by Capsaicin–Sensitive Nerves in *Nippostrongylus Brasiliensis*–Sensitized rats", *J Pharmacol Exp Ther*, 1995, pp. 337–343, vol. 273, No. 1.

J.R. Berrazueta et al., "The Anti–Inflammatory and Analgesic Action of Transdermal Glyceryltrinitrate in the treatment of infusion–related Thrombophlebitis", *Postgrad Med J*, 1993, pp. 37–40, vol. 69.

J.R. Berrazueta et al., "Local transdermal Glyceryl Trinitrate has an Antiinflammatory Action on Thrombophlebitis induced by Sclerosis of Leg Varicose Veins", *Angiology*, 1994, pp. 347–351, vol. 45, No. 5.

P. M. Ridker et al., "Inflammation, Aspirin, and the Risk of Cardiovascular Disease in Apparently Healthy Men", *The new England Journal of Medicine*, 1997, pp. 973–979, vol. 336, No. 14.

A. Franco–Cereceda et al., "Capsaicin–induced Vasodilatation of Human Coronary Arteries in vitro is Mediated by Calcitonin Gene–related Peptide Rather than Substance P or Neurokinin A", *Acta Physiol Scand*, 1989, pp. 575–580, vol. 136.

A. Franco–Cereceda, "Calcitonin Gene–related Peptide and Human Epicardial Coronary Arteries: Presence, Release and Vasodilator Effects", *Br. J. Pharmacol*, 1991, pp. 506–510, vol. 102.

D. Bell et al., "Inhibition by Verapamil and Diltiazem of Agonist–stimulated Contractile Responses in Mammalian Ventricular Cardiomyocytes", *J. Mol. Cell Cardiol*, 1995, pp. 1977–1987, vol. 27.

B.B. Quebbeman et al., "Effect of Calcitonin Gene–related Peptide on Well–developed Canine Coronary Collateral Vasculature", *Journal of Cardiovascular Pharmacology*, 1993, pp. 774–780, vol. 21.

T. Ohmura et al., "Electrophysiological and Mechanical Effects of Calcitonin Gene–related Peptide on Guinea–pig Atria", *Br J Pharmacol*, 1990, pp. 27–30, vol. 100.

Tubaro et al, Arzneim.–Forsch./Drug Res., vol. 45 No. 12, pp. 1298–1302, 1995.*

Tubato et al, Archives of Pharmacology, vol. 348, pp. 670–678, 1993.*

Cross et al, Ann. Intern. Med., vol. 107, No. 4, pp. 526–545 (abstract), 1987.*

* cited by examiner

USE OF AMTOLMETIN GUACYL FOR THE PRODUCTION OF ANTI-INFLAMMATORY DRUGS FOR INTESTINAL INFLAMMATIONS

The present application is the national stage under 35 U.S.C. 371 of international application PCT/IT99/00398, filed Dec. 3, 1999 which designated the United States, and which international application was published under PCT Article 21(2) in the English language.

The present invention relates to the use of amtolmetin guacyl for the production of an anti-inflammatory drug for intestinal inflammations. In the present description amtolmetin guacyl, whose chemical name is 2-metoxyphenyl-1-methyl-5-p-methylbenzoyl-pirrol-2-acetamido acetate, will be also referred to as MED 15.

Inflammation is a primary pathological process involving the passage of the neutrophilic leukocytes through vasal endothelium directed towards the inflamed tissue (1).

The arachidonic acid metabolites have been linked to several inflammatory diseases, including psoriasis (2,3) rheumatoid arthritis (4), asthma (5–8), multiple sclerosis (9), uveitis and IBD (10–14). Prostaglandin can play a role in the inflammatory process, enhancing vasodilatation and formation of oedema; on the other hand lipoxygenase products, in particular LTB4, exert a potent stimulating action on leukocytes: evidence supporting the importance of such metabolites comes from the observation of their increase in the inflamed colon mucus (15–16).

IBD aetiology is obscure, the hypothesised causative agents being antigens of bacterial origin, alimentary intolerance and a defective intestinal barrier. More recently the role of vascularization in Crohn's disease has been further emphasised. Although the IBD triggering event remains unknown, both ulcerative colitis and Crohn's disease in active phase are associated with a non-specific inflammatory reaction, and are characterised by chronic inflammation with overlapping acute inflammatory exacerbation. At the chronic stage macrophages and lymphocytes infiltrate the intestine, whereas in the acute stage the cells migrating in the intestinal mucus are the neutrophils and perhaps the eosinophils.

At present a resolutive therapy for these pathologies is unavailable: the cycloxygenase-inhibiting NSAIDs (17,18) commonly used in the treatment of inflammatory pathologies, not only do not yield an improvement in the disease, but can even cause recurrences in patients in inactive phase. At present, drugs used for the therapy of colitis are corticosteroids, sulfasalazine and 5-ASA. Corticosteroids exert their anti-inflammatory action through the release of a PLA2 endogenous inhibitor named macrocurtain or lipocurtain (19), but possess other biological properties as well, that can be related to their therapeutical effects on IBD: on lymphocyte differentiation, cytokine synthesis and interferon production (20). However, the pharmacological characteristic/property underlying the effectiveness of corticosteroids remains undetermined.

Sulfasalazine and 5-ASA can reduce the inflammation acting as inhibitors of PAF, interleukin 1, TNF, MPO and thus acting as scavengers of the free radicals (21). Hence, as it is the case for corticosteroids, also sulfasalazine and 5-ASA possess other pharmacological properties, unrelated to the eicosanoid production, and for such drugs as well the pharmacological properties underlying their effectiveness is still undetermined.

However, all of these drugs entail serious side-effects that markedly restrict their use in long-term therapies. Therefore it would be desirable to find a product that is both effective for this pathology and devoid of side-effects.

MED 15 is a powerful non-steroidal anti-inflammatory drug (in short NSAID in the following) as amply reported in literature (22–23). Med 15 is the subject matter of the Italian patent IT 1210673. In this regard however, it has to be pointed out that the NSAIDs commonly used as antipyretic, analgesic and anti-inflammatory in a wide spectrum of pathologies, ranging from chronical pain to post-surgery pains to muscular-scheletric pains, rheumatoid arthritis, osteoarthritis, ankylosing spondylitis, to menstrual pains (consequent to prostaglandin release), are well-known to be gastrolesive, in particular at the enteric level.

The present invention is based on the discovery that MED 15 is a NSAID that can be successfully used in Crown's disease, as well as in all intestinal inflammations, in particular colitis with an underlying auto-immune component. Actually, there is experimental evidence proving the protective action exerted by MED 15 on the enteric mucus, in which a marked presence of the intact (i.e., not metabolised) MED 15 molecule was demonstrated, a requirement for ascribing to it a protective effect.

The MED 15 molecular structure includes a vanillic radical responsible for the stimulation of the stomach and intestine capsaicin receptors (24). At the gastric level these receptors are physiologically related to the CGRP neuropeptide, with which they interact for the down-regulation of the acid secretion (25–28); whereas the capsaicinic receptors of the intestine are related to another neuropeptide, VIP, in order to protect the intestinal mucus (29).

VIP (Vasoactive Intestinal Peptide) is a 28 amino acid peptide which is localised in both the central and peripheral nervous system. VIP has various effects on intestinal functions:

1) it stimulates mucosal water, electrolyte and mucus secretion;
2) it is a potent stimulant of duodenal $HCO_3$ secretion;
3) it s involved in peristaltic reflex;
4) it inhibits absorption and has a predominant relaxation action;
5) it plays an inhibitory role on immune cell function.

Several studies demonstrated a decrease of VIP intestinal mucosal content in patients with ulcerative colitis and this alteration seems to be correlated to the degree of mucosal inflammation (see J. Physiol Paris Sorrenti et al 1993; 87(5):307–311).

The released CGRP passes into the bloodstream and reaches other districts, exerting its vasodilator effect. The above mentioned neuropeptides, interacting with the capsaicinic receptors in the two different sites of the gastroenteric apparatus, are responsible of the protective action exerted by MED 15 on the mucus; such effect is obtained at the gastric level by direct action of the CGRP and consequently by NO deriving therefrom (30,31), whereas at the intestinal level VIP acts autonomously, since, unlike CGRP, it does not stimulate NO synthetase. Therefore the action of MED 15 on intestinal inflammation is carried out through the production of VIP, induced by the administration of same MED 15.

In light of the aforementioned it is apparent that in order to obtain a maximum therapeutical effectiveness MED 15 ought to be intaken with an empty stomach to allow saturation of the capsaicinic receptors. Furthermore, on the basis of this mechanism, the need to avoid contemporary intake of anti-H1 drugs (32), known to interfere with the capsaicinic receptors, should be taken into account.

Concerning the MED 15 vasodilator effect, that can be referred as to its mechanism to the CGRP production, it has been previously reported and is incorporated in the present description with reference to the application PCT/IT97/00209.

Therefore, an object of the present invention is the use of MED 15 for the production of an anti-inflammatory drug for intestinal inflammations.

BRIEF DESCRIPTION OF THE DRAWINGS

Six drawing tables are attached to the present description, showing:

FIG. 4 the TNB-induced colitis, wherein FIG. 4a shows the colon weight, FIG. 4b the score and FIG. 4c the MPO;

FIG. 5 the effect of MED 15 and 5-ASA (reference compound) on human ulcerative colitis: FIG. 5a shows severity of intestinal mucosal inflammation and 5b clinical symptomatology;

MATERIALS AND METHODS

Animals

Male Wistar rats, 180±20g quarantined for at least 5days and fasted for 18 h prior to the beginning of the trial (on a grid to avoid coprophagy) with free access to water.

Treatments

Indomethacin-induced Small Intestine Inflammation

The animals were treated with indomethacin (7.5 mg/Kg by subcutaneous administration in $NaHCO_3$ 5%) at T=0 and T=+1 day.

MED 15 (100 mg/Kg per os in 1% CMC) was administered according to two different treatments:

Scheme no. 1: T=0, +1 and 2 days

Scheme no. 2: T=0, +1, +2, +5, +6, +7 days 24 h after the last administration the animals were killed by cervical dislocation; the small intestine (from the pylorus to the ileocecal valve), removed and opened lengthwise, was washed in physiological solution at pH 7.4 for damage evaluation.

Acetic Acid-induced Colitis

Colitis was induced in animals by administration of 5% acetic acid (1.5 ml/rat) in the distal colon lumen with an 8 cm cannula at T=0.

MED 15 (100 mg/Kg per os) was administered at T−48 h, −24 h and −2 h.

24 h after colitis induction, animals were killed by cervical dislocation and the colon removed and washed in physiological solution at pH 7.4, was examined for damage evaluation.

TNB-induced Colitis

Colitis was induced in animals by administration of 15 mg TNB (trinitrobenzosulphonic acid) in 0.25 ml of 30% ethanol in the colon lumen and with an 8 cm cannula at T=0.

MED 15 (100 mg/Kg per os in 1% CMC) was administered to:

T=0, +1, +2, +3 days 5 h after the last administration the animals were killed by cervical dislocation, the colon (8 cm distal portion) removed for damage evaluation.

Damage Evaluation

Considered parameters are:

score;

number of ulcers;

myeloperoxidase (MPO), neutrophil indicator;

malondialdehyde (MDA), oxidative process indicator.

Statistical Evaluation data were evaluated by Student's t-test

Results

Small Intestine Inflammation

Figure 1A:
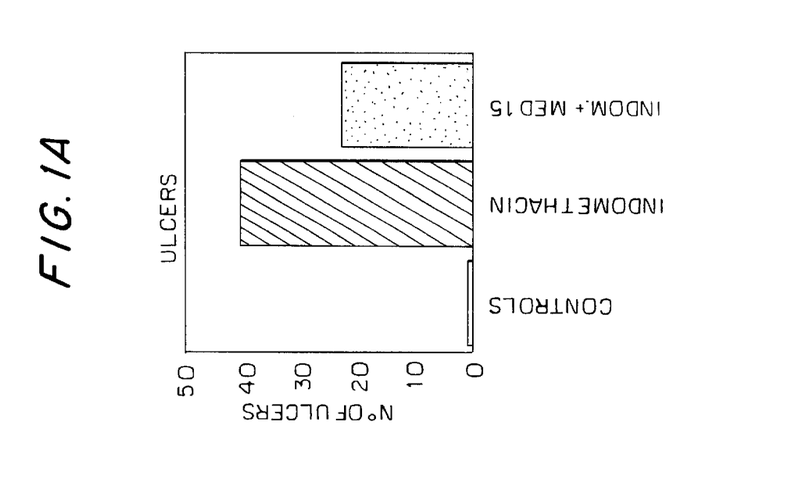
FIG. 1 three diagrams 1a, 1b and 1c respectively, wherein the treatment with MED 15 of an indomethacin-induced small intestine inflammation in acute stage is described.
Figure 1B:
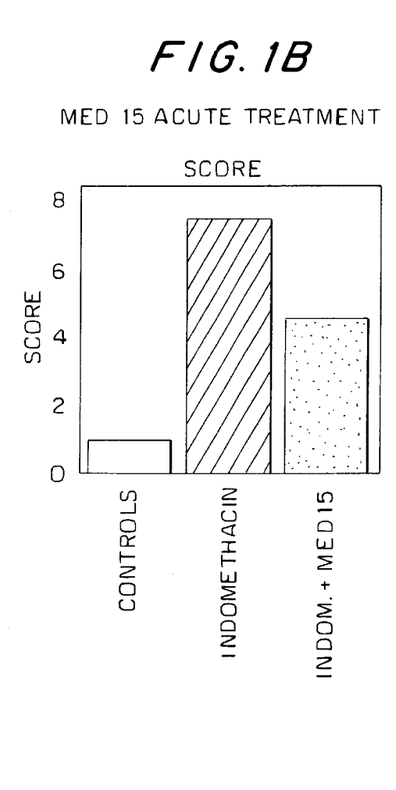
Figure 1C:
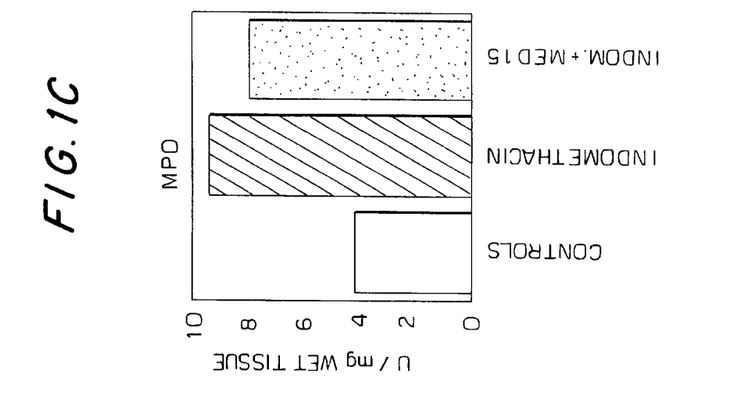

Animals treated according to scheme no. 1 (see page 5, line 36), corresponding to the acute phase treatment with MED 15, showed a 44.3% reduction (see FIG. 1) in the number of ulcers. Concerning the scores, a remarkable reduction is observed in animals treated with MED 15 as compared with the indomethacin controls (4.63±2.73 and 7.62±1.84 respectively).

A diminution of the tissutal levels of MPO was also detected after MED 15 treatment.

Figure 2A:
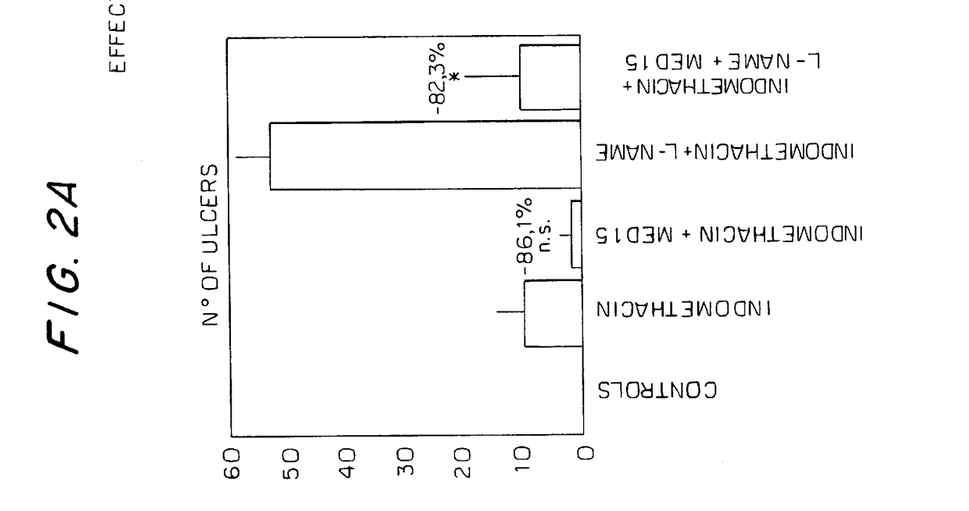
FIG. 2 the intestinal inflammation induced by a prolonged treatment with indomethacin treated with MED 15, and also the effect of L-NAME, wherein in FIG. 2a the number of ulcers, and in FIG. 2b the score is reported.
Figure 2B:
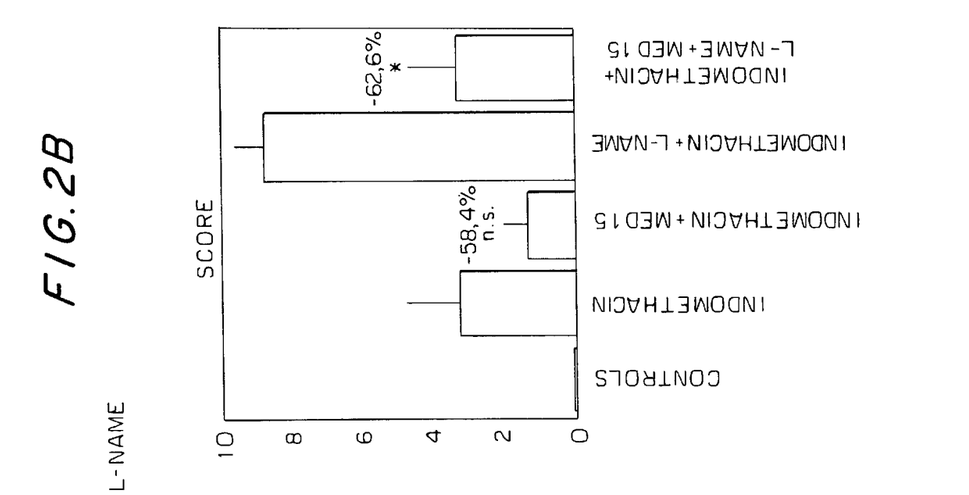

Consequent to the treatment according to scheme n° 2 (see page 5, line 37), in which MED 15 was administered for prolonged times, a consistent reduction of all parameters was observed. As to the number of ulcers, an 86.1% decrease was observed the score value showed a 58.4% decrease (see FIG. 2). All this shows that by prolonging the MED 15 treatment the effectiveness thereof enhanced, which constitutes an entirely new feature for a NSAID, since usually drugs belonging to this group are known to be gastrolesive.

Acetic Acid-induced Colitis

Figure 3:
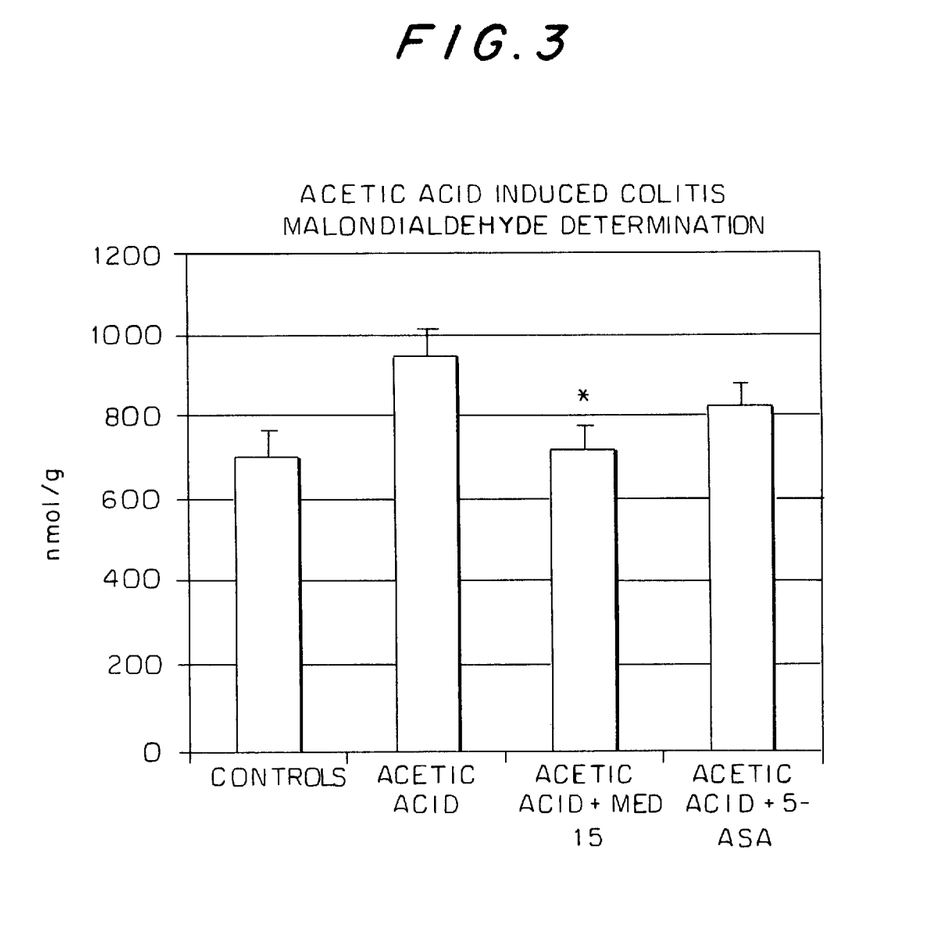
FIG. 3 a diagram reporting the malondialdehyde determination in the case of acetic acid-induced colitis.

This model caused extremely severe lesions and the seriousness of the pathological picture affected the malondialdehyde levels as well (acetic acid controls 949±66 nmoles/g; acetic acid+MED15 719±60 nmoles/g) (see FIG. 3).

TNB-induced Colitis

Figure 4A:
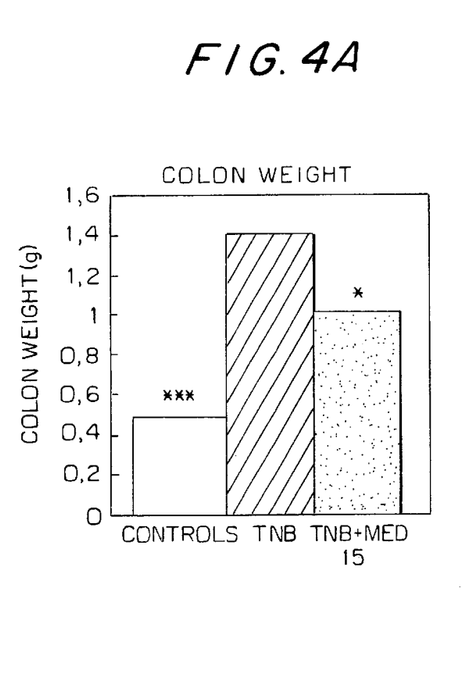
Figure 4B:
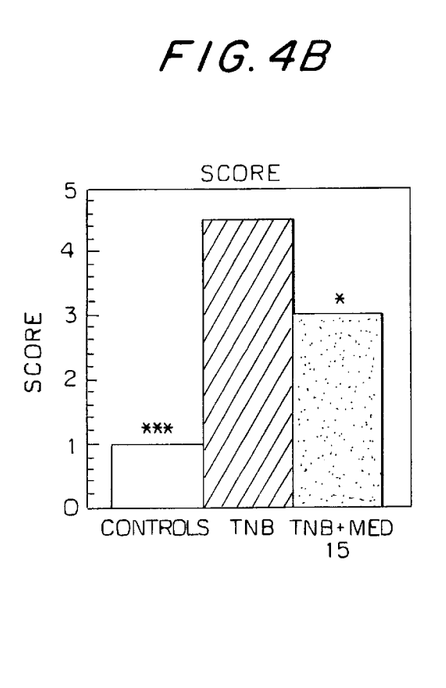
Figure 4C:
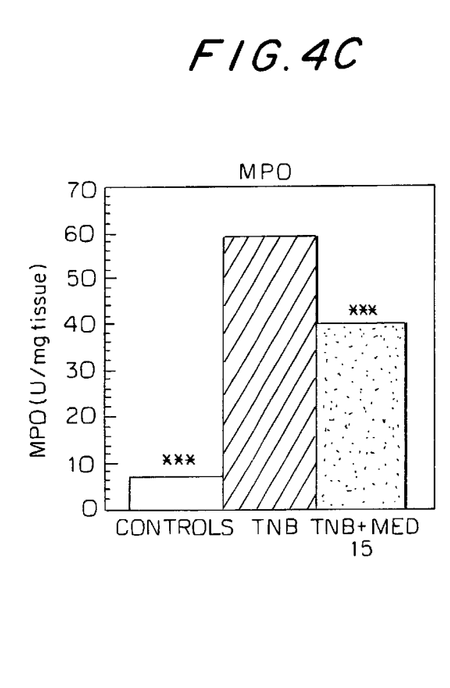

MED 15 effectiveness on the various inflammation parameters was evaluated, yielding positive results in each case: the colon walls weight (−28.6%), as well as the score (−35.2%) and the myeloperoxidase levels (−33.1%) is significantly reduced compared to the TNB control (see FIG. 4).

CLINICAL TRIAL

A double-blind, controlled, randomized study was carried out in patients affected by two simultaneous pathologies: ulcerative colitis and osteoarticolar disease (osteoarthritis, rheumatoid arthritis, extra-articular rheumatism).

Patients and Treatment 20 patients were divided into 2 homogeneous groups of 10 patients each (Group A and Group B):

Group A was treated with 5-aminosalicylic acid 1200 mg/day and placebo

Group B was treated with 5-aminosalicylic acid 2300 mg/day and MED 15 1200 mg/day The therapy had a duration of 60 days.

Clinical Evaluation

The following clinical evaluations were performed at the beginning of the study ($T_0$), $T_{15}$, $T_{30}$, and $T_{60}$ (end of therapy):

1) endoscopic examination of intestinal mucosa 2) annotation of symptomatology referred by the patients.

The severity of these parameters was expressed by a score as follows:

1) mild
2) moderate
3) severe.

Figure 5A:
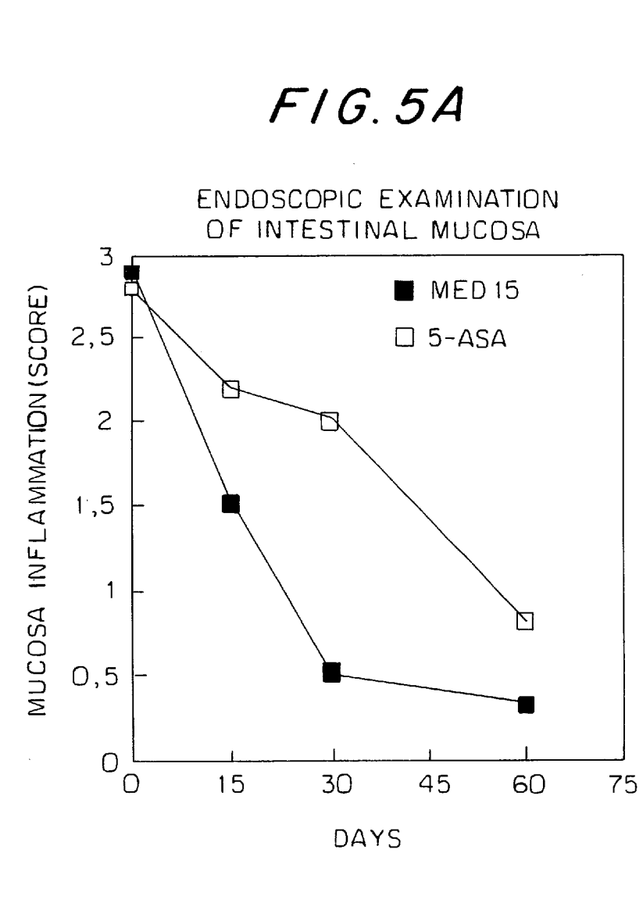
Figure 5B:
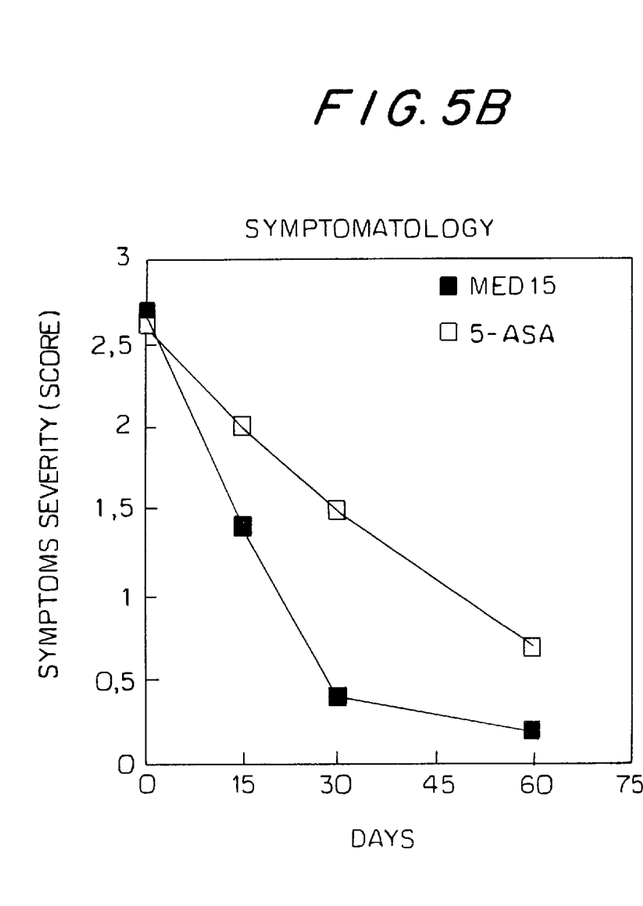

The results of the study show that MED 15 was more effective than 5-ASA in ulcerative colitis of patients (FIG. 5) who were also affected by pre-existing osteoarticular pathology. The clinical parameters observed demonstrated that MED 15 may be administered with advantage in the treatment of intestinal inflammatory conditions at a dosage of 1200 mg/day. Healing time was dramatically reduced compared to 5-ASA. MED 15 can be administered for intestinal inflammation treatment in a 600–1200 mg/day dosage The present invention further relates to the MED 15 effects as anti-platelet agent, a thrombotic and vasodilator, anti-inflammatory and analgesic agent in the treatment of infarcted patients and of patients at risk of, or having a cerebral ictus of thrombotic type.

INHIBITORY EFFECT OF MED 15 ON PLATELET AGGREGATION

MED 15 showed inhibitory effects on in vitro platelet aggregation in rat and also in induction of the $TXB_2$ plasma level inhibition, comparable to those of the acetylsalicylic acid (ASA). The following pharmacological tests were carried out in order to show the MED 15 inhibitory effects on platelet aggregation.

MATERIALS AND METHODS
1. Chemicals

Collagen, arachidonic acid sodium chloride, acetyl salicylic acid and carboxymethylcellulose (CMC) [Sigma Chimica, Milan]; amtolmetin guacyl [Alpha Chemicals Italiana, Bergamo]; sodium citrate [Merck, Germany].
2. Animals Male New Zealand rabbits, 2000–3000 g [Stefano Morini, S. Polo D'Enza, RE Italy], quarantined for 5 days prior beginning of the trial (anti-piatelet effect). Male Wistar rats, 250±20 g [IFFA CREDO, Italy] randomized, divided into groups of 5 animals each and fasted for 16 h prior to treatment (thromboanemia determination).

Animals were fed standard laboratory chow with free access to water and were maintained for the entire duration of the trial under animal house conditions of 22±2 C.° temperature, relative humidity 55±10% and 12-h light-dark cycle.
3. Determination of Platelet Aggregation on Rabbit PRP (Plasma Rich in Platelets)

Blood was intracardially collected from rabbits, using as anticoagulant sodium citrate at a final concentration of 0.38% and centrifuged for 15' at 150 g in order to obtain a plasma rich in platelets (PRP). PRP was used at a concentration of $3.5 \times 10^8$ platelet/ml. MED 15 and reference products were incubated with the PRP for 3' at 37 C° prior to addition of the aggregating agent. Platelet aggregation induced by arachidonic acid, sodium salt [TAC (threshold aggregation concentration): 140 μm] and collagen (TAC: 28 μg/ml) was measured using an aggregometer (Chronolog model 500) according to the Born's method (Borg G. V. R. Nature 1962; 194: 927–929) and was expressed as inhibition percentage with respect to the agonist mean response.
4. Thromboanemia Determination in Rat The animals received per OS 100 mg/kg (1.5 ml/rat) MED 15 and (acetyl salicylic acid) suspended in 1% CMC, and controls received the vehicle only. Blood samples, collected intracardially 3 h after treatment, were incubated for 60' at 37 C° and centrifuged for 10' at 3600 rpm. Tromboxane content was determined in the serum thus obtained using a RIA kit [Amersham TRK780]. The results obtained can be evaluated with reference to the following tables and figures.

Figure 6A:
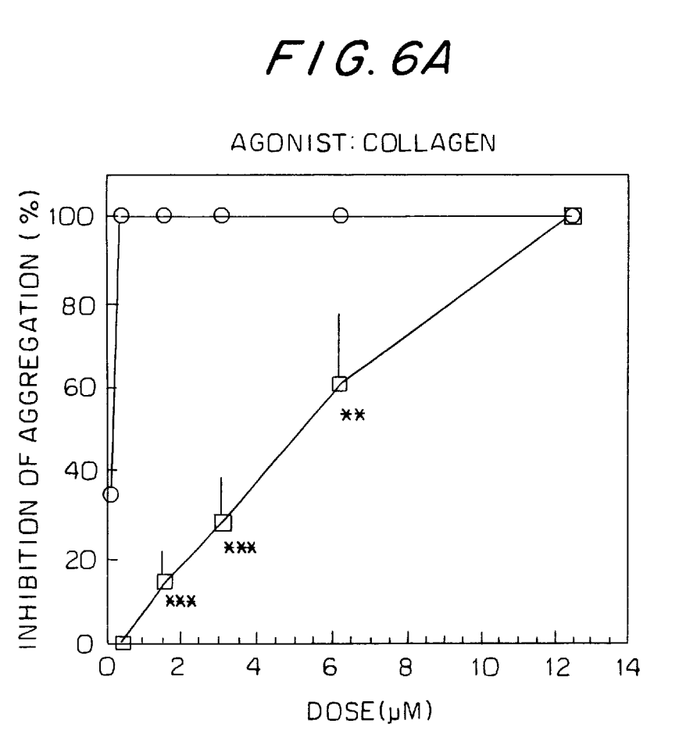
FIG. 6 the MED 15 and TOLMETIN (indicated as reference drug) effects on platelet aggregation using as agonists collagen (FIG. 6a) and arachidonic acid (FIG. 6b) respectively.
Figure 6B:
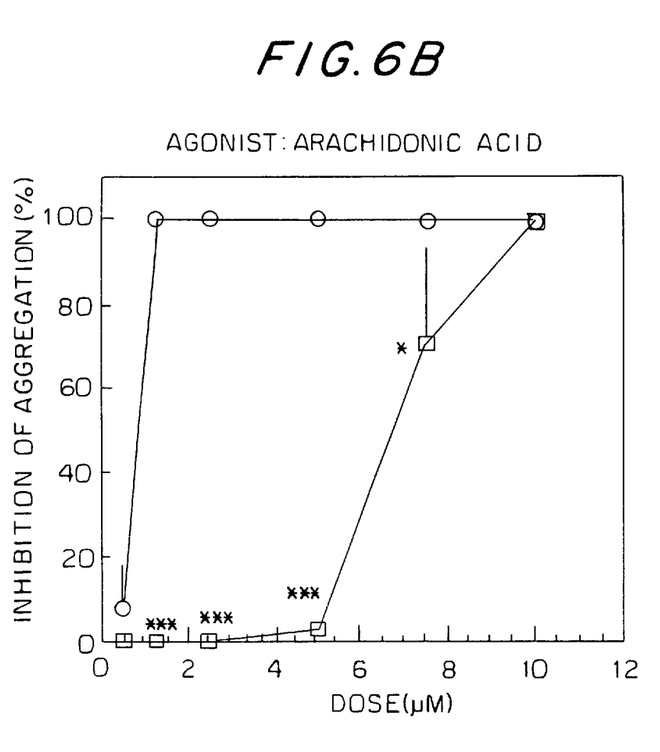

FIG. 6 shows inhibition (%) of rabbit platelet aggregation comparing the MED-15 effect with that of tolmetin at different dosages using collagen and arachidonic acid as agonists (FIGS. 6a, 6b, respectively). The following tables 1 and 2 show the MED 15 anti-platelet effect in vitro versus ASA (acetyl salicylic acid) using arachidonic acid (table 1) and collagen (table 2) as agonists.

TABLE 1

In vitro anti-platelet effect of MED 15 versus ASA
Agonist: arachidonic acid sodium salt

| Substance | Dose (μM) | Inhibition (%) |
|---|---|---|
| MED 15 | 5.0 | 100.0 |
|  | 2.5 | 100.0 |
|  | 1.25 | 100.0 |
|  | 0.5 | 7.7 |
| ASA | 100.0 | 100.0 |
|  | 50.0 | 83.3 ± 16.7 |
|  | 25.0 | 0 |

TABLE 2

In vitro anti-platelet effect of MED 15 versus ASA
Agonist: collagen

| Substance | Dose (μM) | Inhibition (%) |
|---|---|---|
| MED15 | 0.39 | 100.0 |
|  | 0.10 | 34.3 |
|  | 0.05 | 0 |
| ASA | 100.0 | 100.0 |
|  | 50.0 | 70.4 ± 14.9 |
|  | 25.0 | 33.7 ± 2.1 |
|  | 12.5 | 18.4 ± 10.5 |

Tables 3 and 4, reported hereinafter, show the results of additional test and prove the effect of MED 15 on $TXB_2$ (thromboxane) plasma levels in rat compared with acetyl salicylic acid and with controls and the kynetics of the percent inhibition of $TXB_2$ plasma levels in rat.

TABLE 3

Effects of MED 15 and ASA on $TXB_2$ plasma levels in rat

| Groups | $TXB_2$ ng/ml ± S.E. | inhibition % | P |
|---|---|---|---|
| Controls | 174.1 ± 42.6 | — | — |
| ASA | 2.9 ± 1.1 | 98.3 | 0.003 |
| MED15 | 14.3 ± 1.3 | 91.8 | 0.004 |

TABLE 4

Kinetics of percentual inhibition of $TXB_2$ plasma levels in rat

| Groups | % inhibition | P |
|---|---|---|
| Controls | — | — |
| MED15 0.75 h | 93.2 | 0.0001 |
| 1.5 h | 90.8 | 0.0001 |
| 3.0 h | 91.4 | 0.0001 |
| 24.0 h | 49.2 | 0.032 |

This effect is prolonged, extending over a 24-h interval. The aforestated proves that MED 15 has inhibitory effects on blood platelet aggregation.

Therefore, a further object of the present invention is the use of MED 15 for the production of a drug counteracting platelet aggregation in the blood of patients requiring it, i.e. of those intolerant to acetyl salicylic acid and to NSAIDs. This use may be also advantageous in patients in further need of an anti-inflammatory and analgesic treatment. To obtain the maximum drug effectiveness, MED 15 administration should take place with an empty stomach and without the concurrent administration of anti-H, drugs.

The administration dosage of MED 15 capable of showing its anti-aggregating properties is in the range 300–600 mg/day; the drug can be administered alone or with usual pharmaceutically tolerable excipients in the form of pharmaceutical compositions.

Effect of MED 15 on thrombophlebitis.

MED 15 can be used in thrombophlebitis treatment as well, in particular in puerperal thrombophlebitis.

Usually with the term thrombophlebitis the inflammation of a vein associated with thrombus formation is understood. In this case in the vascular bed near the thrombus a peculiar situation subsists, concomitantly producing pain and inflammation. In order to treat a patient suffering from thrombophlebitis, the pain and the inflammation need to be treated at the same time. NSAIDs are among the drugs most frequently used for pain and inflammation treatment, by virtue of their specific anti-inflammatory and analgesic properties (33,34,35). However, the mere use of an NSAID among those known in the state of the art is insufficient to completely treat thrombophlebitis. Actually, there is the concurrent need to exert a thrombotic effect, usually met by administration of streptokinase or urokinase, or of tissutal plasminogen activator (tPA). Moreover, exerting at least locally a vasodilator effect proves extremely useful for increasing the chances of clearing the vessel of the thrombus. This vasodilator effect facilitates the clearing of the thrombus from the vessel itself, widening the vessel section. Finally, once the vessel is cleared of the thrombus, the further need to avoid the occurrence of similar pathological conditions can be satisfied by use of anti-platelet agents, so as to avoid platelet adhesion onto the vessel walls. Aspirin, heparin and low molecular weight heparinoids are commonly used for this purpose.

In light of the aforestated it is evident that, in order to completely a thrombophebitis five goals must be reached: pain and inflammation treatment, vasodilatation, thrombolysis and prevention of a further platelet aggregation. According to the state of the art the aforementioned is attainable using at least four types of drug: a NSAID (for pain and inflammation), aspirin or heparin-like substances (anti-aggregation), urokinase-like substances (thrombotic effect) and a vasodilator. Further, taking into account the well-known gastrolesivity of the NSAIDs, the most frequently used drugs for pain and inflammation treatment, concomitant administration of a gastroprotective drug, i.e. a proton pump inhibitor like omeprazole or an $H_2$-receptor antagonist like famotidine. Hence, a substance simultaneously exerting analgesic and anti-inflammatory, as well as anti platelet aggregation and vasodilator properties, without showing gastrolesive effects would prove extremely useful.

MED 15 anti platelet aggregation properties have already been pointed out and proved.

MED 15 vasodilator effect has already been shown with respect to its action mechanism. In short, it can be stated that MED 15 administration triggers the CGRP production in the stomach, with subsequent release of the peptide in the bloodstream, and the possibility of reaching several organs. Therefore, the CGRP-derived vasodilator effect takes place in each reached organ. This CGRP effect is also apparent in human coronary artery dilation (36, 37, 38, 39, 40). In this regard, it has to be pointed out that the vasodilator effect exerted by CGRP per se can be considered as known by the state of the art and in the literature, whereas a CGRP production by the MED 15 action mechanism is completely unknown.

A final consideration regarding the use of MED 15 as NSAID in light of its anti-inflammatory and analgesic properties, is that MED 15 demonstrates a gastroprotective effect not exhibited by other NSAIDs. This fact, once more explainable by its action mechanism, has the further advantage that no concomitant administration of gastroprotective drugs (such as proton pump inhibitors like omeprazole or $H_2$-receptor antagonists like famotidine) is necessary. Doubtlessly, the gastroprotective effect exerted by MED 15 enables a safe and prolonged drug administration, during puerpuerium as well as in presence of pathological conditions entailing the risk of a thrombophlebitis.

Therefore, the use of a single drug, MED 15, allows the treatment of the following factors, that require a concurrent treatment in case of a thrombophlebitis, and specifically prevention of pain and inflammation, vasodilatation and excessive platelet aggregation. Moreover, by virtue of MED 15 gastroprotective properties, an additional administration of a gastroprotective drug becomes superfluous.

Therefore, a further object of the present invention is the use of MED 15 for the production of a drug for the treatment of thrombophlebitis, in particular for puerpuerial thrombophlebitis. For a better effectiveness, administration to a patient should take place on empty stomach and without concomitant intake of $H_1$-receptor antagonists.

MED 15 administration dosage ranges from 600 to 1200 mg/day; the drug can be administered alone or in a pharmaceutical composition, associated with the usual pharmaceutically tolerable excipients.

Vasodilator properties of MED 15.

By virtue of its vasodilator properties linked to the release of CGRP in the bloodstream, MED 15 can also be used in the treatment of other patients, as hereto reported. The primary use of MED 15, as for any NSAID, is for pain and inflammation treatment; however, the unexpected properties mainly due to its action mechanism, allow an advantageous MED 15 administration to patients benefiting from a vasodilator effect in addition to the anti-inflammatory and analgesic properties. MED 15 treatment is suitable for infarcted patients, or for patients that had, or are at risk of a cerebral ictus of thrombotic type and at the same time are in need of an NSAID treatment. CGRP is well known to produce vasodilatation in the cerebral artery, as well as in the coronary artery.

Therefore, a further object of the present invention is the use of MED 15 for the production of a drug for the treatment of pain and inflammation in an infarcted patient.

For maximum effectiveness, the administration should take place at empty stomach and without the concomitant intake of $H_1$-receptor antagonists.

A further class of patients that may be treated by virtue of MED 15 vasodilator properties is that of patients that had, or are at risk of ictus of the cerebral vessels. For a better understanding of the possibilities of treating this new class of patients with MED 15, it is necessary to draw a distinction between two fundamental ictus typologies. Cerebral ictus can be generically defined as a discontinuity inside a cerebral vessel. This discontinuity can have two origins: a thrombotic origin (i.e., the vessel is obstructed by a thrombus) or a haemorrhagic origin (i.e. the vessel bursts).

Thrombotic ictuses are treated with anti-platelet substances, whereas haemorrhagic ictuses are treated with anti-haemorrhagic substances. Thus, the two treatments are antithetical. MED 15 can be used in the treatment of patients suffering from cerebral ictuses of thrombotic origin, not tolerating NSAIDs and in need of an anti-inflammatory antalgic treatment. The vasodilator effect of the cerebral vessels is advantageous to the patients.

Therefore, a further object of the present invention is the use of MED 15 for the production of a drug for the treatment of pain and inflammation in a patient suffering from, or at risk of, a cerebral ictus of thrombotic type. The administration of the drug, for a maximum effectiveness thereof, should take place at empty stomach and without the concomitant intake of $H_1$-receptor antagonists.

MED 15 administration dosage ranges from 600 to 1200 mg/day; the drug can be administered alone or as a pharmaceutical composition, associated with the usual pharmaceutically tolerable excipients.

REFERENCES

1. Dore M., Simon S. I., Hughes B. J., Entman M. L., Smith C. W. P-selectin-and CD18-mediated recruitment of canine. neutrophils under conditions of shear stress. Vet Pathol 1995;32:258–68.
2. Greaves M. W., Camp R. D. R. Prostaglandis, leukotrienes, phospholipase, platelet activating factor, and cytokines: An integrated approach to inflammation of human skin: Arch Dermatol Res 1988,280:S33–41.
3. Fry I. Psoriasis. Br J Dermatol 1988;119:445–461.
4. Belch J. J. F. Eiconsanoids and rheumatology: inflammatory and vascular aspects. Prostaglandins LeukotEssent Fatty Acids 1989;36:219–234.
5. Ford-Hutchinson A. W. Leukotrienes. Their formation and roles as inflammatory mediators. Fred Proc 1985;44:25–29.
6. Kay A. B. Leukocytes in asthma. Immunol Invest 1988;17:690–705.
7. Raeburn D. Eicosanoids, epithelium and airway reactivity. Gen Pharmacol 1990;21:11–16.
8. Leff A. R. Toward the formulation of a theory of asthma. Prospect Biol 1990;33:292–302.
9. Mayer M. Effect of calcium ionophore A23187 and of leukotrienes $B_4$ and $C_4$ on the adherence of mononuclear leukocytes in multiple sclerosis. Folia Biologica (Praha) 1988;34:10–17.
10. Stenson W. F. Arachidonic acid metabolites in inflammatory bowel disease. Adv Inflamm Res 1988;12:215–222.
11. Schumert R., Tower J., Zipser R. D. Role of eicosanoids in human and experimental colitis. Dig Dis Sci 1988;33:58S–64S.
12. Goetzel E. J., Burral B., Baud L., Scriven K., Levine J., Koo C. L. Generation and recognition of leukotriene mediators of hypersensitivity and inflammation: Dig Dis Scrl1988;33:36S–40S.
13. Lauritsen K., Laursen L. S., Bukhave K., Rask-Madsan J. Inflammatory intermediaries in inflammatory bowel disease. Int J Colon Dis 1989;4:75–90.
14. Rask-Madsen J., Bukhave K., Laursen L. S., Lauritsen K. Eicosanoids in inflammatory bowel disease. Physiology and pathology. In The Cell Biology of Inflammation in the Gastrointestinal Tract. T. J. Peters Eds., Corners Pubblications, Hull 1990:255–271.
15. Boughton-Smith N. K., Hawkey C. J., Whittle B. J. Biosynthesis of lipoxygenase and cyclooxygenase products from [14C]-arachidonic acid by human colonic mucosa. gut 1983;24:1176–82.
16. Sharon P., Stenson W. F. Enhanced synthesis of leuotriene B4 by colonic mucosa in inflammatory bowel disease. Gastroenterology 1984;86:453.60.
17. Gould S. R., Brash A. R., Conolly M. E., Lennard-Jones J. E. Studies of prostaglandis and sulphasalazine in ulcerative colitis. Prostaglandins Med 1981;6:165–82.
18. Rampton D. S., Sladen G. E. Prostaglandin systhesis inhibitors in ulcerative colitis 1981;21:417–25.
19. Blackwell G. J., Carnuccio R., Di Rosa M., Flower R. J., Parente L., Persico P. Macrocortin: a polypeptide causing the anti-phospholipase effect of glucocorticoids. nature 1980;287:147–9.
20. MacDermott R. P., Stenson W. F. Alterations of the immune system in ulcerative colitis and Crohn's disease. Adv Immunol 1988;42:285–328.
21. Fretland D. J., Djuric S. J., Gaginella T. S. Eicosanoids and inflammatory bowel disease: regulation and prospects for therapy. Prostagkandins Leukot Essent Fatty Acids 1990;41:215–233.
22. Arrigoni-Martell E. 2-[2-[1-methyl-5-(4-methylbenzoyl) pyrrol-2-yl]acetamido]acetic acid 2-methoxyphenyl ester. MED15. Drugs of the Future 1989;14:963–65.
23. Tubaro E., Belogi L., Mezzadri C. M., Ruco L., Stoppacciaro A. Studies on the gastric tolerability of the new non-stereoidal anti-inflammatory drug amtolmetin guacyl. Arzeim Forsch Drug Res 1995;45:1298–1302.
24. Szallasi A., Blumberg P. M. Resiniferatoxin and its analogs provide novel insights into the pharmacology of the vanilloid (capsaicin) receptors. Life Sci 1990;47:1399–408.
25. Peskar B. M., Wong H. C., Walsh J. M., et al A monolocal antibody to calcitonin gene-related peptide abolishes capsaicin-induces gastroprotection. Eur J Pharmacol 1993;250:201–3.
26. Ren J., Young R. L., Lassiter D. C., et al. Calcitonin gene-related peptide mediates capsaicin-induced neuroendocrine responses in rat antrum. Gastroenterology 1993;104:485–491.
27. Kinoshita Y., Inui T., Chiba T. Calcitonin gene-related peptide: a neurotransmitter involved in capsaicin-sensitive afferent non-mediated gastric mucosal protection. J Clin Gastroenterol 1993;17:S27–32.
28. Holzer P., Peskar B. M., Peskar B. A., et al. Release of calcitonin gene-related peptide induced by capsaicin in the vascularly perfused rat stomach. Neurosci Lett 1990;108:195–200.
29. Yagy K., Takehara K., Kitamura M., et al. Effects of pituitary adenylate cyclase activating polypeptide-27 on alkaline secretory and mucosal ulcerogenic responses in rat duodenum. Life Sciences 1998;63:317–325.
30. Holzer P., Watcher C., Heinemann A., et al. Sensory nerves, nitric oxide and NANC vasodilatation. Arch Int Pharmacodyn Ther 1995:239:67–79.
31. Holzer P., Watcher C., Jocic M., et al. Vascular bed-dependent roles of peptide CGRP and NO. JPhysiol 1994;480:575–585.
32. Mathison R., Davison J. S. Regulation of jejunal arterioles by capsaicin-sensitive nerves in Nippostrongylus brasiliensis-sensitized rats. J Pharmacol Exp Ther 1995;273:337–343.
33. Berrazueta J. R., Poveda J. J., Ochoteco J., Amado J. A., Puebla F., Salas E., Sarabia M. "The anti-inflammatory and analgesic action of transdermal gliceryltrinitrate in the treatment of infusion-related thrombophlebitis". Postgrad Med J 1993;69:37–40.
34. Berrazueta J. R., Fleitas M., Salas E., Amado J. A. Poveda J. J., Ochoteco J., Sanchez de Vega M. J., Ruiz de Celis G. "Local transdermal glyceryltrinitrate has an anti-inflammatory action on thrombophlebitis induced be sclerosis of leg varicose venis". Angiology 1994;45:347–351.

35. Ridker P. M., Cusham M., Stampfer M. J., Tracy R. P., Hennekens C. H. "Inflammation, aspirin, and the risk of cardiovascular disease in apparently healthy men". N Engl. J Med 1997;336:973–979.

36. Franco-Cereceda A., Rudehill A. "Capsaicin-induced vasodilation of human coronary arteries in vitro is mediated by calcitonin gene-related peptide rather than substance P or neurokinin A". Acta Physiol Scand 1989;136:575–580.

37. Franco-Cereceda A. "Calcitonin gene-related and human epicardial coronary arteries: presence, release and vasodilator effects". Br J Pharmacol 1991;102:506–10.

38. Bell D., McDermott B. J. "Inhibition by verapamil and diltiazem of agonist-stimulated contractile responses in mammalian cardiomyocytes". J Mol Cell Cardiol 1995;27:1977–87.

39. Quebbeman B. B., Dulas D., Altman J., Homans D. C., Bache R. J. "Effect of calcitonin gene-related peptide on well-developed canine coronary collateral vasculature". J Cardiovasc Pharmacol 1993;21:774–80.

40. Ohmura T., Nishio M., Kigoshi S., Muramatsu I. "Electrophysiological and mechanical effect of calcitonin gene-related peptide on guinea-pig atria". Br J Pharmacol 1990;100:37–30.

What is claimed is:

1. A method for the treatment of intestinal inflammations comprising administering to a patient in need thereof an effective amount for said treatment of amtolmetin guacyl.

2. The method of claim 1, wherein said patient is one suffering from ulcerative colitis or Crohn's disease.

3. The method of claim 1, wherein said amtolmetin guacyl is administered on an empty stomach and without concurrent administration of anti-$H_1$ drugs.

4. A method in accordance with claim 2, wherein said amtolmetin guacyl is administered on an empty stomach and without concurrent administration of anti-$H_1$ drugs.

5. A method of inducing production of VIP or stimulation of stomach and intestine capasaicin receptors in the intestinal tract of a patient in need of said therapy, comprising administering to said patient an effective amount for said therapy of amtolmetin guacyl.

6. The method of claim 5 wherein said patient is one who is suffering from colitis or Crohn's disease.

7. The method of claim 5, wherein said effective amount is in the range from about 600 to about 1200 mg/day.

* * * * *